United States Patent [19]

Philpott

[11] Patent Number: 5,229,271
[45] Date of Patent: Jul. 20, 1993

[54] METHOD OF TESTING OF HAIR GROWTH SUBSTANCES ON HAIR FOLLICLES PREPARED BY MECHANICALLY SEVERING OF HAIR SHAFT

[75] Inventor: Michael Philpott, Cambridge, England

[73] Assignee: Chesebrough-Pond's USA Co., Division of Conopco, Inc., Greenwich, Conn.

[21] Appl. No.: 626,928

[22] Filed: Dec. 13, 1990

[30] Foreign Application Priority Data

Dec. 19, 1989 [GB] United Kingdom ............... 8928634

[51] Int. Cl.$^5$ .................. C12Q 1/02; C12N 5/00; A01N 1/02
[52] U.S. Cl. .................. 435/29; 435/240.21; 435/260; 435/1
[58] Field of Search ............ 424/70; 435/29, 240.2, 435/240.21

[56] References Cited

FOREIGN PATENT DOCUMENTS 2612939  9/1988  France .

OTHER PUBLICATIONS

Rogers et al. J. Investigative Dermatology, 89, (4) pp. 369-373 (1987).
Buhl et al., J. Investigative Dermatology, 92, (3) pp. 315-320 (1989).
M. Philpott et al., Journal of Science, 93, (3), pp. 409-418 (1989).
European Search Report and Annex.

Primary Examiner—Michael G. Wityshyn
Assistant Examiner—Jane A. Williams
Attorney, Agent, or Firm—Milton L. Honig

[57] ABSTRACT

A method of testing a substance for its ability to promote, maintain, increase or arrest hair growth, or influence hair pigmentation comprise the steps of:
 i. isolating a viable hair follicle from skin, without damaging the hair bulb;
 ii. maintaining the isolated, viable hair follicle in a nutrient medium;
 iii. contacting the isolated hair follicle in said medium with a test substance, and
 iv. assessing the response of the hair follicle to said test substance.

8 Claims, No Drawings

METHOD OF TESTING OF HAIR GROWTH SUBSTANCES ON HAIR FOLLICLES PREPARED BY MECHANICALLY SEVERING OF HAIR SHAFT

FIELD OF THE INVENTION

The invention relates to a method of testing, in particular to a method of testing substances or compositions containing them for their ability to promote, maintain, increase or arrest hair growth.

BACKGROUND

The Hair Follicle and the Hair Growth Cycle

The hair follicle is composed of an epithelial component, the matrix and outer root sheath enclosing the hair shaft and a dermal component, the dermal papilla within the bulb. Hair growth is effected by the division of the hair follicle basal cells and in the mammal, this is cyclical. Three distinct stages of hair growth can be identified, namely:

i. an active stage known as anagen, during which the hair follicle penetrates deep into the dermis with the cells of the bulb dividing rapidly and differentiating to form the hair, ii. a regressive stage known as catagen, which is heralded by the cessation of mitosis, and during which the follicle regresses upwards through the dermis and hair growth ceases, and iii. a resting stage known as telogen, in which the regressed follicle contains a small secondary germ with an underlying ball of tightly packed dermal papilla cells.

The initiation of a new anagen stage is revealed by rapid proliferation in the germ, expansion of the dermal papilla and elaboration of basement membrane components. The hair cycle is then repeated many times until, as a consequence of the onset of male pattern baldness, most of the hair follicles spend an increasing proportion of their time in the telogen stage, and the hairs produced become finer, shorter, and less visible; this is known as terminal to vellus transformation.

Loss of hair on the human head, particularly that which results in male pattern baldness, is a natural process often associated with advancing age. Baldness occurring in young people, particularly men, can give the impression that age is advancing faster than it really is.

Baldness can also result from a disorder of the skin known as Alopecia areata.

Since time immemorial, man has striven to maintain the appearance of youth with potions and lotions to preserve skin condition and also to reverse the natural ageing process. This has applied also to hair loss, with the result that many hair restorers, hair lotions and the like have been applied to the scalp in an attempt to slow or arrest hair loss or to increase hair growth.

In order to determine whether any substance at least has the potential to restore or otherwise enhance hair growth on the scalp, or even to retard growth, it is first necessary to carry out clinical tests involving applying the substance to the skin of a test animal, for example the rat, or to human volunteers. Although ultimately, the results of in vivo clinical tests are required to support patenting and/or commercial exploitation, such tests are time consuming and costly to perform. Accordingly, there exists a need for an in vitro screening test to determine rapidly whether or not a substance at least has the potential for enhancing or retarding hair growth.

Attempts have in the past been made to isolate hair follicles and then to cultivate them to maintain viability, in order to use them to determine the activity of potential hair growth substances, by studying their biochemical behaviour following contact with such substances. An example of this is referred to by Rogers et al., in a paper entitled "Cultivation of Murine Hair Follicles as Organoids in a Collagen Matrix", published in the Journal of Investigative Dermatology, 89, No. 4, (1987), 369–379, who described the isolation and cultivation of functionally intact mouse hair follicles. In this technique, follicles were isolated by collagenase digestion of dermis from five-day-old mice and purified by differential centrifugation and filtration. Purified follicles were then cultured in a collagen matrix.

In a further technique described by Buhl et al. in a paper entitled "Minoxidil stimulates mouse vibrissae follicles in organ culture", published in the Journal of Investigative Dermatology, 92, No. 3, (1989), 315–320, a method of testing the hair growth stimulating drug, Minoxidil, is described. Here, whisker follicles were dissected from three-day-old mice and cultured in Dulbecco's Modified Eagles medium, with added fetal bovine serum and Gentamicin, with or without Minoxidil, in the presence of 10% $CO_2$ at 37° C., and follicle function was assessed by measuring the uptake of radiolabelled cysteine, glycine and or thymidine, by quantifying changes in follicle-hair shaft length and with histology. The authors reported that culture of control follicles (without Minoxidil) showed macroscopic changes including kinking of the hair shafts and bending of the follicles. Furthermore, necrosis was evident in the differentiating epithelial elements forming the cuticle, cortex and inner root sheath. Although culture of similar follicles in the presence of Minoxidil reduced or eliminated these abnormalities and caused them to grow longer than controls over a 3 day period, it is clear that the dissection technique originally employed (using jeweller's forceps operating on separated whisker pads) caused sufficient damage to the individual whisker follicles to detract from their usefulness in testing potential hair growth promoters. Accordingly, there remains a need for a more delicate yet productive technique for removing hair follicles from the skin in an undamaged state, such that they can then reliably be used to assess, by culture while in a fully viable state, the potential activity of substances for promoting or retarding hair growth promoters.

SUMMARY OF THE INVENTION

We have now made a careful and detailed study of the histology of the hair follicle and the surrounding tissue in which it is situated, and we have observed that where the hair shaft passes through the dermis, the degree of adhesion between the hair shaft and the surrounding dermal tissue is such that the hair bulb is invariably damaged if it is pulled away from its seating in the subcutaneous fatty layers below the skin surface. We have accordingly concluded that it is this damage which impairs subsequent response of the separated hair follicle to culture in a suitable nutrient medium, a factor which renders uncertain the validity of experiments relying on the culture of hair follicles separated by ordinary dissection, for testing the influence of substances on hair growth.

While trying other methods of separating intact and undamaged hair follicles from the skin, we devised a successful technique which involved first severing the hair shaft at the dermal-subcutaneous fat interface, so that the intact hair bulb subsequently could be removed without damage. The fact that the hair shaft was severed provided a useful point of reference when measuring accurately hair elongation (if any) during culture, as it was apparent that this did not affect the absolute rate of hair growth. The further observation that hair follicles removed from skin using our special technique grew straight, without abnormalities and without necrosis or developing biochemical abnormalities, added further confidence to our belief that separation of the hair follicle without damage to the hair bulb, was paramount to the success of a method of testing the response of substances on promoting or retarding hair growth, for which we seek a monopoly.

Furthermore, the separation from the skin of the hair follicle without damage to the hair bulb by this new technique could also facilitate the study of substances on other aspects of the developing hair, such as pigment formation. Thus, for example this technique has made possible, without resort to live animal testing, the study of agents which are believed to promote or inhibit melanocyte activity.

DEFINITION OF THE INVENTION

Accordingly, the invention provides a method of testing a substance for its ability to promote, maintain, increase or arrest hair growth, or to influence hair pigmentation which method comprises the steps of:
 i. isolating a viable hair follicle from skin, without damaging the hair bulb;
 ii. maintaining the isolated, viable hair follicle in a nutrient medium;
 iii. contacting the isolated hair follicle in said medium with a test substance, and
 iv. assessing the response of said hair follicle to said test substance.

DISCLOSURE OF THE INVENTION

Isolation of the Hair Follicle From Skin

The method of testing according to the invention includes the important step of isolating hair follicles having an undamaged hair bulb from skin, preferably from human skin, by microdissection, but preferably without the enzymic pretreatment advocated by other workers in this field. It is important to note that enzymic pretreatment, using collagenase in accordance with the teaching of Rogers et al., referred to earlier, should be avoided if the viability and biochemical functioning of the hair follicle is to be maintained in an unimpaired state following removal from the skin.

As has already been stated, separation of hair follicles with an intact, undamaged and fully functioning hair bulb, even without enzymic pretreatment, is virtually impossible by normal microdissection methods, in view, of the degree of adhesion that exists between the hair follicle and the skin tissue where it passes through the dermis. Thus, separation of dermis from the hair follicle almost invariably causes damage to the hair bulb.

The critical step of separating the hair follicle with intact undamaged hair bulb from the subcutaneous fatty tissue in which it is situated accordingly involves severing the hair shaft of the follicle at a point below the epidermis or skin surface, so as to leave the hair bulb intact and undamaged while still bearing a portion of the hair shaft.

Preferably, the hair shaft of the follicle is severed at the dermal-subcutaneous fat interface.

Any suitable cutting instrument can be employed to sever the hair shaft in this manner, but a keratotome or a scalpel are preferred.

The hair bulb with a hair shaft stump attached is then isolated from the skin by mechanically separating the hair from loosely adhering subcutaneous fat which normally surrounds the hair bulb. This is achieved after the dermis or upper layer of the skin has been separated and removed, to avoid damaging the hair bulb as it is pulled away.

The hair bulb together with the hair shaft stump attached, is then transferred in an otherwise undamaged and fully functioning, viable state to a nutrient medium.

Culture of the Isolated Hair Follicle

The hair follicles isolated by the technique described herein are transferred to a suitable culture medium for subsequent testing of substances that can then influence their future development.

The procedure now to be described represents a preferred method of culture and testing of hair growth and is purely illustrative of the principles set forth herein. It is accordingly to be understood that culture media and measurement technique other than those described are suitable and that the monopoly sought is not limited solely to this preferred method of culture and measurement techniques.

In accordance with the preferred method of culture, isolated hair follicles were maintained in 500 $\mu$l of Williams E medium at 37° C. in an atmosphere of 5% $CO_2$+95% air in individual wells of a 24 multiwell dish (Corning), which permitted detailed measurements to be made of the length of individual hair follicles.

Williams E medium is available from FLOW Laboratory under Catalogue No. 12-502. The formula of Williams E medium is described by Williams GM, et al., in Experimental Cell Research 69 (1971) at page 106.

Hair shaft length measurements made on these follicles, using a Nikon Diaphot inverted binocular microscope with eye piece measuring graticules, show that over 4 days in culture, the follicles significantly increased in length.

Furthermore, photographic evidence showed that this increase in length is not associated with any disruption of hair follicle architecture. In particular, the length increase can be seen to be attributed to the production of keratinised hair shaft.

It is also possible to employ several different biochemical and morphometric analyses to study the effect of a substance on the viable hair follicle. For example, autoradiography using tritiated thymidine shows that in freshly isolated hair follicles, the typical pattern of cell division is taking place, with the majority of thymidine uptake occurring in the matrix cells of the hair follicle bulb, adjacent to the dermal papilla. Over 4 days'-maintenance, this pattern remains constant.

These observations, both histological and biochemical on hair follicles separated by our special technique and cultured in Williams E medium without the addition of a hair growth promoter as a test substance, confirmed the validity of our technique, since abnormality of growth and biochemical response were totally absent. From this we concluded that the method of testing described in here represents a valid technique for testing a response of substances on the growth and other changes in hair follicles.

Experimental Testing of Hair Growth Promoters or Retarders

The techniques described herein can be employed to test substances or composition containing them, for their ability to perform either as hair growth promoters for initiating, maintaining or increasing hair growth, or as hair growth retarders for reducing or arresting hair growth, as an alternative to using a depilatory.

The response of an isolated hair follicle to a test substance, can accordingly be assessed by using one or more of the methods described herein for validating the isolation technique and culture of hair follicles in a suitable growth medium, such as Williams E medium. Culture in the suitable growth medium will therefore provide a control system for comparison with culture in the same medium containing the test substance.

Convenient methods for assessing response of a test substance versus the control over a four day culture period accordingly include:

1. Measuring the increase (if any) of the length of the hair follicle; and
2. Measuring the increase (if any) of [methyl$^3$H] thymidine uptake;

The method of testing as disclosed herein is not restricted to these two parameters, as the change in any physical, chemical or biochemical property of the isolated hair follicle can be employed to assess the response of a test substance.

EXAMPLES

The results obtained following use of the method in accordance with the invention are illustrated as follows.

Hair follicles isolated from viable human female skin were maintained in Williams E medium containing a supplement of 1% Foetal Calf Serum (FCS), in accordance with the method described and defined herein, Hair growth was measured over a 72 hour period and rates of [methyl-$^3$H] thymidine uptake were recorded over a period of 3 hours incubation. In each case, measurements were made on at least 6 hair follicles from each sample of skin.

Statistical analysis was carried out using Student't-test to compare differences between follicles maintained with 1% FCS (control) and treated follicles maintained in the presence of TGF-$\beta$ or IGF-1 (test treatments).

The results obtained are tabulated as follows

| Treatment | Hair Growth mm over 72 hr | [$^3$H] thymidine pmoles/$\mu$g DNA/3 hr |
|---|---|---|
| 1% FCS (control) | 0.81 ± 0.04 | 2.57 ± 0.35 |
| TGF-$\beta$ (10 ngml$^{-1}$) | 0.57 ± 0.03* | 1.56 ± 0.21** |
| IGF-1 (30 ngml$^{-1}$) | 0.76 ± 0.05 | 4.04 ± 0.39** |

*$P < 0.001$
**$P < 0.05$

From the results it can be deduced that TGF-$\beta$ significantly reduces hair growth and also significantly reduces uptake of [methyl-$^3$H] thymidine, whereas IGF-1 significantly stimulates uptake of [methyl-$^3$H] thymidine, although this is not reflected as a change in linear growth rate.

This suggests that TGF-$\beta$ can be used as depilatory agent by virtue of its ability to reduce hair growth compared with the control, whereas IGF-1 nevertheless has potential as a hair growth stimulant.

I claim:

1. A method of testing a substance for its ability to promote, maintain, increase or arrest hair growth, or influence hair pigmentation, which method comprises the steps of:
   i. isolating a hair follicle from skin;
   ii. maintaining the isolated hair follicle in a nutrient medium;
   iii. contacting the isolated hair follicle in said medium with a test substance; and
   iv. assessing the response of the hair follicle to said test substance;

wherein isolating of the hair follicle from skin comprises mechanically severing the hair shaft of the follicle below the epidermis without enzymatic pretreatment of the follicle and skin, thereby to avoid damage to the hair bulb.

2. A method of testing according to claim 1, in which isolating the hair follicle from skin includes the step of severing the hair shaft of the follicle at the dermal-subcutaneous fat interface.

3. A method of testing according to claim 2, in which the hair shaft is severed using a keratotome or scalpel.

4. A method of testing according to claim 1, in which isolating the hair follicle from skin includes the further step of mechanically separating the hair bulb from surrounding subcutaneous fat subsequent to separation of the dermis.

5. A method of testing according to claim 1, in which the nutrient medium comprises Williams E. medium.

6. A method of testing according to claim 5, in which the nutrient medium comprises foetal calf serum.

7. A method of testing according to claim 1, in which the response of the isolated hair follicle to the test substance is assessed by measuring any increase of the length of the hair follicle.

8. A method of test according to claim 1, in which the response of the isolated hair follicle to the test substance is assessed by measuring any increase of (methyl-$^3$H) thymidine uptake by the hair follicle.

* * * * *